United States Patent [19]

Boettcher

[11] Patent Number: 4,967,010

[45] Date of Patent: Oct. 30, 1990

[54] PREPARATION OF SYMMETRIC AND ASYMMETRIC MONOACETALS OF AROMATIC 1,2-DIKETONES

[75] Inventor: Andreas Boettcher, Nussloch, Fed. Rep. of Germany

[73] Assignee: BASF Aktiengesellschaft, Ludwigshafen, Fed. Rep. of Germany

[21] Appl. No.: 410,042

[22] Filed: Sep. 19, 1989

[30] Foreign Application Priority Data

Oct. 6, 1988 [DE] Fed. Rep. of Germany ....... 3834029

[51] Int. Cl.$^5$ ............................................. C07C 45/64
[52] U.S. Cl. .................................................... 568/315
[58] Field of Search ................................ 568/315, 592

[56] References Cited

U.S. PATENT DOCUMENTS

| | | | |
|---|---|---|---|
| 4,144,156 | 3/1979 | Kuesters et al. | 568/315 |
| 4,190,602 | 2/1980 | Brunisholtz et al. | 568/315 |

FOREIGN PATENT DOCUMENTS

| | | | |
|---|---|---|---|
| 1580967 | 12/1980 | United Kingdom | 568/315 |
| 1580968 | 12/1980 | United Kingdom | 568/315 |

*Primary Examiner*—James H. Reamer
*Attorney, Agent, or Firm*—Keil & Weinkauf

[57] ABSTRACT

Symmetric and asymmetric monoacetals of aromatic 1,2-diketones are prepared by a novel process, in a nonpolar solvent in the presence of a urea derivative as the catalyst.

7 Claims, No Drawings

PREPARATION OF SYMMETRIC AND ASYMMETRIC MONOACETALS OF AROMATIC 1,2-DIKETONES

The present invention relates to a novel process for the preparation of symmetric and asymmetric monoacetals of aromatic 1,2-diketones in an nonpolar solvent in the presence of a urea derivative as a catalyst.

Compounds of the type comprising the cyclic and acyclic, symmetric benzil 1,1-acerals are known photoinitiators and are described in, for example, DE-A 22 32 365, DE-A 23 37 813 and EP 85 031. Derivatives of 9,9'-phenanthrenequinone dimethyl acetal or of acenaphthenequinone have pharmacological activity.

For the preparation of the monoacetals of benzil and of phenanthrenequinone, Kuhn et al. (Chem. Ber. 94, (1961), 2258) used barium oxide (barium hydroxide) and methyl iodide in dimethylformamide. The same workers convert anhydrous ninhydrin in methanol in the presence of 5% strength by weight of methanolic hydrochloric acid with dimethyl sulfite into the stable substance 1,1dimethyl acetal. This principle of synthesis has been applied to acetals of benzil. Here, the aromatic 1,2diketone is reacted with a sulfurous ester in the presence of an anhydrous acid in a primary monoalcohol as thionyl the solvent or with a sulfurous ester produced in situ from chloride in excess alcohol, which is described in, for example, DE-A 23 37 813, DE-A 23 65 497, DE-A 23 65 852, AT 331 237 and ES 508 476.

In other publications, trialkyl orthoformates are proposed as alkylating agents. For example, benzil is converted with trimethyl orthoformate in excess methanol in the presence of sulfuric acid into the corresponding dimethyl ketal (Chem. Abstr. 96, 34871 and JP 56 128-729). According to K. C. Rice (Synthesis 1988, 233), better results are obtained in nitromethane using trifluoromethanesulfonic acid and the ortho-ester.

Acenaphthenequinone can be converted with p-toluenesulfonic acid, zinc chloride, zinc chloride/concentrated sulfuric acid or iron(III) sulfate/concentrated sulfuric acid in absolute alcohol into the corresponding ketal (J. Tsunetsugu, J. Chem. Soc. Perkin Trans.I 1986, 1965).

A different method is adopted by G. LiBassi et al. (EP 85 031): benzoins are reacted in dimethylformamide with sulfuryl chloride to give the corresponding dichloride, which is converted into the symmetric acetal with sodium alcoholate in alcohol.

Common to all the above mentioned processes is the fact that
1. exclusively symmetric acetals
2. which are prepared with acidic catalysts.

It is known from the literature that acetals and ketals can be cleaved back into the corresponding carbonyl compounds and alcohols in the presence of acidic catalysts in good to very good yields (cf. for example Houben-Weyl, VII/1, 423; VII/2a, 790; Organic Synth. Coll. Vol. III 217, 731 (1955)). Hence, the ketals can be prepared in acceptable yields only if the alkylating reagent is present in excess and no acid is liberated during working up. Furthermore, all processes mentioned above have the disadvantage that they give poorly reproducible yields and require high temperatures and long reaction times when they are scaled up.

These problems are solved if the reaction is carried out from the outset in an alkaline medium. In this way, aromatic benzils can be converted into the 1,1-acetals in high yield in the presence of alkali metal alcoholates with arylsulfonic esters or alkyl sulfates, this being disclosed in DE-A 26 16 382, DE-A 26 16 408 and DE-A 26 16 588. This process also permits, in particular, the preparation of asymmetric ketals, which are not obtainable by other methods. In the processes described to date for the preparation of ketals of aromatic 1,2-diketones, the property of the solvent used is particularly important; in all cases, only polar solvents, e.g. dioxane, dimethylformamide or methanol, are preferred, because not only are they optimal for the nucleophilic substitution or the alkylation reaction but furthermore can readily be removed during working up of the reaction mixtures by mixing with water. However, this procedure is unsatisfactory from the point of view of pollution of waste water and, as a rule, expensive purification processes must be carried out subsequently in order to remove the solvents from the waste water. It is generally known that a water-miscible organic solvent can be removed from the aqueous phase only by expensive methods, such as distillation or extraction. Frequently, moreover, azeotropic mixtures are formed with water, making complete recovery impossible.

Another aspect of the solvent problem is apparent in the thionyl chloride/methanol system. The alkylating agent is produced in the reaction in excess methanol The corrosive gases $SO_2$ and HCl are formed; furthermore, the formation of methyl chloride cannot be ruled out.

In the process described in German Patent No. 2,616,382, 2,616,408 and 2,616,588, corrosive gases cannot form. The use of dioxane and dimethylformamide is preferred. However, the latter solvent reacts with the sodium methylate/dimethyl sulfate at very high temperatures with formation of dimethylformamide dimethyl acetal. The alkylating agent is thus consumed for this reaction In DE-C 26 16 382, aromatic solvents, such as benzene, toluene, xylene or o-dichlorobenzene, are also mentioned as being suitable. In the case of the benzil dimethyl ketal obtainable from benzil, the total yield in toluene as a solvent is, however, less than 50%. Benzene, xylene and o-dichlorobenzene behave in a similar manner.

Even the addition of solubilizers for alkali metal alcoholates, for example ethylene glycol dimethyl ether, diethylene glycol monobutyl ether, polyethylene glycol dimethyl ether or Pluriol ® E 1000 (polyethylene glycol from BASF), results in a poor yield of benzil dimethyl ketal and the formation of dimethyl ether. This is due to the fact that, in toluene and in the presence of the stated solubilizers, the alkylation of sodium methylate by dimethyl sulfate is preferred. When polar solvents are used, the reaction proceeds in the desired direction.

It is an object of the present invention to provide an environmentally compatible process for the preparation of symmetric monoacetals of aromatic 1,2-diketones in a recoverable nonpolar organic solvent, which process also gives high yields.

We have found that this object is achieved by the use of special urea derivatives as catalysts in the alkylation reaction in nonpolar organic solvents This not only increases the yields but also suppresses the side reactions and reduces the reaction times.

The present invention relates to a process for the preparation of symmetric and asymmetric 1,1-acetals of aromatic 1,2-diketones of the general formula I

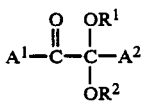

where $A^1$ and $A^2$ are straight-chain or branched alkyl or alkoxy radicals of 1 to 6 carbon atoms, which are identical, different or bonded to one another, or aromatic radicals carrying halogen or phenyl radicals and $R^1$ and $R^2$ are identical or different, unsubstituted or substituted, straight-chain or branched alkyl radicals of 1 to 10 carbon atoms, from the corresponding aromatic 1,2-diketones of the general formula II

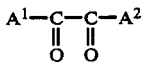

wherein the 1,2-diketones, in a nonpolar aprotic solvent, are reacted with an alkylating agent

an alcoholate

where n and m are integers of from 1 to 3, X is a radical of a monobasic to tribasic acid and M is a metal of main groups 1 to 3 of the periodic table of the elements, in the presence of a urea derivative of the general formula III or IV

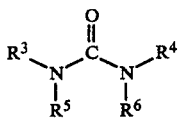

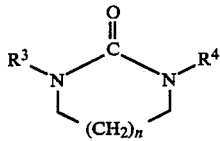

or of a mixture of III or IV, where n is from 0 to 3 and $R^3$, $R^4$, $R^5$ and $R^6$ are identical or different, straight-chain or branched alkyl radicals of 1 to 6 ca or hydrogen, as a catalyst and from $-20$ to $+ 100°$ C.

Regarding the starting materials, the following may be stated:

The aromatic diketones used in this process are known and are prepared, for example, by the process described in DE-A 36 24 146, by oxidation of the corresponding benzoins.

Suitable aromatic diketones of the general formula II are in particular those in which the aryl radicals, which may be bonded to one another, independently of one another are each phenyl which is unsubstituted or not more than trisubstituted by alkyl or alkoxy of 1 to 6 carbon atoms, halogen or phenyl. Examples of aromatic 1,2-diketones which may be used for this process are benzil and substituted benzils, such as 4,4,-dimethylbenzil, 4,4,-diisopropylbenzil, 4,4,-diphenylbenzil, 2,2,-dimethoxybenzil, 4-methylbenzil, 3-methoxybenzil, 2,2'-dimethylbenzil, 4-chloro-4'-phenylbenzil, 4,4,-dichlorobenzil, 3,3,-dibromobenzil, 2,4,2,,4,-tetramethylbenzil, 2,4,6-trimethylbenzil and 2,4-dichloro-4,-methylbenzil. Examples of aromatic 1,2-diketones in which the aryl radicals are bonded to one another and which may be used for this process are unsubstituted or substituted phenanthrenequinone, acenaphthenequinone or 1,2-acenathrenequinone. These o-quinones can be prepared by processes known from the literature and by the process described in J. Chem. Soc., Perkin Trans. I 1986, 1965.

Alkylating agents which are suitable for the process are of the stated formula $(R^1)_nX$ and are esters of monobasic to tribasic acids, in particular of acids containing a sulfur, a phosphorus or a halogen atom. Examples are the esters of sulfuric acid, of sulfurous acid, of phosphoric acid and of phosphorus acid, the esters of hydrohalic acids such as chlorides, bromides and iodides, and of the aliphatic and aromatic sulfonic acids, such as the mesylates, tosylates, brosylates and benzene sulfonates. The sulfates, halides and sulfonates are particularly suitable, of which the sulfates are preferred. The ester radical $R^1$ is an unsubstituted or substituted hydrocarbon radical of 1 to 10 carbon atoms. Suitable radicals and substituents are described in DE-A 26 16 588.

Examples of alkylating agents which may be used for this process are dimethyl sulfate, diethyl sulfate, dihexyl sulfate, diallyl sulfate, dicrotyl sulfate, di-($\beta$-phenylethyl) sulfate, di-($\beta$-phenylallyl) sulfate, di-($\beta$-methoxyethyl) sulfate, di-($\beta$-phenoxyethyl) sulfate, di-(methylthioethyl) sulfate or di-($\beta$-phenylthioethyl) sulfate, benzyl bromide, allyl bromide, methyl benzenesulfonate, ethyl benzenesulfonate, methyl p-toluenesulfonate, ethyl p-toluenesulfonate and the o-/p-mixture of the corresponding toluenesulfonates. For example, the readily obtainable o-/p-mixtures of methyl toluenesulfonate or dimethyl sulfate are preferred.

The alcoholates used are alternatively alcoholates corresponding to the alkylating agent (for symmetric acetals) or those which do not correspond (for asymmetric acetals), having radicals $R^2$, for example an ethylate, such as sodium ethylate or potassium ethylate, when dimethyl sulfate is used or, for example, sodium ethylate when allyl bromide is used. Otherwise, the above statements for the radicals $R^1$ are applicable in general 30 terms to the type of radicals $R^2$. The alcoholates of sodium and of potassium are preferred and are preferably used in solid crystalline form or suspended in the corresponding organic solvent.

The catalysts used are urea derivatives of the general formula III or IV. Examples of suitable derivatives of the formula III are dimethylurea, diethylurea, tetramethylurea, tetraethylurea, tetrabutylurea and mixtures thereof. Dimethylurea, tetramethylurea tetrabutylurea are preferred.

Examples of suitable derivatives of the formula IV are N,N'-propyleneurea, N-methylpropyleneurea, N,N'-dimethylpropyleneurea, N,N'-ethyleneurea, N-methylethyleneurea, N,N'-dimethylethyleneurea and mixtures thereof. N-methylpropyleneurea and N,N'-dimethylpropyleneurea are preferred.

However, it is possible to use mixtures of the urea derivatives of the formulae III and IV. The urea derivatives are used in amounts of from 0.5 to 50, preferably from 5 to 30, % by weight, based on the particular diketone used.

Of the organic solvents or solvent mixtures, only nonpolar solvents are suitable. The Handbook of Chemistry and Physics (62nd edition), page C-700, gives examples. Preferred solvents among these are again the aromatic solvents which have a boiling point in the range from 60 to 140° C. The amount of solvent should advantageously be such that the reaction mixture is readily stirrable after all reactants have been combined. This is generally the case when the solvent accounts for not less than about half the reaction mixture.

The novel reaction of the 1,2-diketones with the alkylating agent and alcoholate is carried out in general at from -20 to 100° C., preferably at 20 to 40° C. The level and constancy of the internal temperature is important for the success of the reaction. It depends on the reactivity of the anion formed from the diketone and from the alcoholate. In the case of diketones of moderate reactivity, for example 4,4'-dimethylbenzil, it should not exceed 35–40° C. In the case of ketones which react very slowly with the alcoholate/alkylating agent, measuring must be effected under temperature control. In general, however, the reaction is complete within a few minutes and in most cases comes to an end as soon as the reactants have been combined. In this respect, the present process differs substantially from the method described in DE-A 26 16 382, DE-A 26 16 408 and DE-A 26 16 508, the said method requiring long subsequent stirring times.

Theoretically, 1/n mole of alkylating agent of the formula $(R^1)_nX$ defined above is reacted with one mole of 1,2-diketone and 1/m mole of alcoholate of the formula $(R^2O)_mM$ likewise defined above, n and m corresponding to n and m, respectively, in the formula of the alkylating agent and the alcoholate used, in order to produce the asymmetric 1,1-acetals of the aromatic 1,2-diketones. In general, however, it is preferable to use some reactants in excess amounts in order to achieve complete conversion. Thus, it is possible to use from 1/n to 10/n moles or more, preferably from 1/n to 4/n moles, of alkylating agent and from 1/m to 10/m moles or more, preferably from 1/m to 4/m moles, of alcoholate per mole of 1,2-diketone.

In an advantageous embodiment of the invention, the process is carried out by a method in which the alcoholate is introduced into a reaction mixture consisting of the aromatic 1,2-diketone, the alkylating agent, the catalyst and the solvent. The alcoholate may be added directly as a solid substance or in the form of a suspension, for example in toluene, xylene or o-dichlorobenzene.

The process is most advantageously carried out by continuously metering in the powdered, crystalline alcoholate under temperature control. The addition of water or protic solvents, for example alcohol, interferes with or inhibits the alkylation.

After the end of the reaction, which can very readily be determined, for example, by thin layer chromatography or gas chromatography, any residues of dimethyl sulfate are destroyed by adding a base, such as ethanolamine, ammonium hydroxide or aqueous hydroxide solution, or by hydrolysis of excess sodium alcoholate or potassium alcoholate. It is of course necessary to ensure that the reaction mixture does not become acidic in pH, since otherwise hydrolysis of the 1,1-acetal to the corresponding diketone may occur.

Working up of the reaction mixture and isolation of the reaction product can be carried out by conventional methods, such as precipitation, extraction or distillation. In a possible procedure, for example, the excess alkylating agent is destroyed, after which the toluene is removed, phase separation is carried out and the water-immiscible acetal is purified by crystallization or distillation. However, in this procedure it is essential that the solvent used for the reaction is water-immiscible and forms an azeotropic mixture with water. The acetal isolated in this manner is obtained in analytically pure form. The process has the advantage that the solvent used in the reaction and the catalyst can be substantially recovered from the corresponding phases by traditional methods.

EXAMPLE 1

Preparation of benzil dimethyl ketal

Method A:

84 g of benzil, 15 g of N,N'-propyleneurea and 65 ml of dimethyl sulfate were dissolved in 400 ml of toluene at room temperature. 5 times 7.5 g of sodium methylate were added to the pale yellow solution at a rate such that the internal temperature did not exceed 30° C. After the end of the addition, 20 ml of 20% strength by weight sodium hydroxide solution were added dropwise and the reaction mixture was heated to 60° C. under atmospheric pressure. After 20 minutes, the pressure was reduced to 300 mbar and an azeotropic mixture of 20% by weight of water/80% by weight of toluene was first distilled off, followed by pure toluene. After the addition of 400 ml of 10% strength by weight aqueous hydroxide solution, the remaining toluene was distilled off. At 70° C., phase separation was then carried out and the organic phase was recrystallized from isopropanol/water.

Yield: 96 g (94%) of colorless needles of melting point 63–65° C.

Method B:

The crude benzil dimethyl ketal obtained in the phase separation was subjected to fractional distillation under 10 mbar over a short packed column. After a small first fraction of residual water, pure benzil dimethyl ketal passes over as an oil of boiling point of 165° C/10 mbar; this oil crystallizes on standing to give colorless needles.

Yield: 98 g (96%).

Method C:

The crude benzil dimethyl ketal obtained in the phase separation was introduced slowly, in the form of a melt, into a mixture of 720 ml of water and 80 ml of methanol, the said ketal being precipitated in the form of fine colorless prisms. It was filtered off under suction, washed with 20:1 water/methanol and then dried under reduced pressure.

Yield: 95 g (93%).

EXAMPLES 2 to 15

Variation of the catalyst

Example 1, Method A, was modified by replacing the catalyst N,N'-propyleneurea with the catalysts of the formula III shown in Table 1. The following yields were obtained:

TABLE 1

| Example No. | Catalyst | Yield of isolated BDK [%] |
|---|---|---|
| 2 | — | 48 |
| 3 | Ethylene glycol dimethyl ether | 58 |
| 4 | Diethylene glycol monomethyl ether | 4 |
| 5 | Diethylene glycol monoethyl ether | 50 |
| 6 | Diethylene glycol monobutyl ether | 8 |

TABLE 1-continued

| Example No. | Catalyst | Yield of isolated BDK [%] |
| --- | --- | --- |
| 7 | 1,2-Propanediol | 42 |
| 8 | Pluriol ® E 1000 | 53 |
| 9 | Dimethylformamide | 72 |
| 10 | N,N'-Dimethylpropyleneurea | 97 |
| 11 | N-Methylpropyleneurea | 92 |
| 12 | N,N'-Ethyleneurea | 85 |
| 13 | N-Methylethyleneurea | 82 |
| 14 | N,N'-Dimethylethyleneurea | 96 |
| 15 | Tetramethylurea | 88 |

In Examples 2 to 8, the reaction time selected was doubled. In Examples 3 to 6, spontaneous, exothermic reaction occurred after an inhibition phase of different lengths, the said reaction involving vigorous evolution of gas in the case of 8 and 9.

EXAMPLE 16

Preparation of benzil 1-ethyl acetal

Benzil was reacted with dimethyl sulfate and sodium ethylate in the presence of N,N'-dimethylpropyleneurea similarly to Example 1, Method A. After phase separation, the pure desired product was obtained as a yellowish oil, which gradually crystallized after standing for one week.
Yield: 79%, m.p. 53–54° C.

EXAMPLES 17 to 19

Preparation of further dialkyl acetals

The following dialkyl acetals were synthesized by methods similar to the method described in Example 1:

TABLE 2

| Example | Dialkyl acetal | Method | Catalyst | Yield |
| --- | --- | --- | --- | --- |
| 17 | Phenanthrenequinone dimethyl acetal | A Ethyl acetate/ hexane | N-Methylpropyleneurea | 65 |
| 18 | 2,2-Dimethoxyacenaphthylene-1-(2H)-one | A Hexane | Tetramethyl urea | 83 |
| 19 | 2-Ethoxy-2-methoxy-acenaphthylene-1-(2H)-one | Isopropanol/water | N,N'-Dimethyl-propyleneurea | 85 |

I claim:

1. A process for the preparation of a symmetric or an asymmetric 1,1-acetal of an aromatic 1,2-diketone of the general formula I

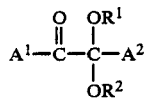

where $A^1$ and $A^2$ are aromatic radicals and $R^1$ and $R^2$ are identical or different, unsubstituted or substituted, straight-chain or branched alkyl radicals of 1 to 10 carbon atoms, from the corresponding aromatic 1,2-diketone of the general formula II

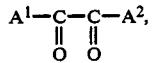

wherein the 1,2-diketone, in a nonpolar aprotic solvent, is reacted with an alkylating agent

an alcoholate

where n and m are integers of from 1 to 3, X is a radical of a monobasic to tribasic acid containing a sulfur, a phosphorous or a halogen atom, and M is a metal of main groups 1 to 3 of the periodic table of the elements, in the presence of a urea derivative of the formula III or IV

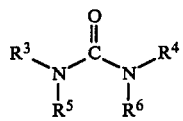

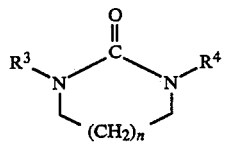

or of a mixture of III or IV, where n is from 0 to 3 and $R^3$, $R^4$, $R^5$ and $R^6$ are identical or different, straight-chain or branched alkyl radicals of 1 to 6 carbon atoms or hydrogen, as a catalyst at from $-20$ to $+100°$ C.

2. A process as described in claim 1, wherein a water-immiscible, nonpolar organic solvent is used.

3. A process as described in claim 1, wherein dimethyl urea or tetramethylurea or a mixture thereof is used as the catalyst of the general formula III.

4. A process as claimed in claim 1, wherein ethyleneurea, propyleneurea, one of their mono- or bis-(N-$C_1$–$C_6$-alkyl) derivatives or a mixture of these compounds is used as the catalyst of the formula IV.

5. A process as described in claim 2, wherein dimethylurea or tetramethylurea or a mixture thereof is used as the catalyst of the formula III.

6. A process as described in claim 2, wherein ethyleneurea, propyleneurea, one of their mono- or bis-(N-$C_1$$C_6$-alkyl) derivatives or a mixture of these compounds is used as the catalyst of the general formula IV.

7. A process as described in claim 1 wherein $a^1$ and $A^2$ are independently of one another, phenyl which is unsubstituted or not more than trisubstituted by alkyl or alkoxy of 1 to 6 carbon atoms, halogen or phenyl.

* * * * *

UNITED STATES PATENT AND TRADEMARK OFFICE
CERTIFICATE OF CORRECTION

PATENT NO. : 4,967,010

DATED : October 30, 1990

INVENTOR(S) : Andreas BOETTCHER

It is certified that error appears in the above-identified patent and that said Letters Patent is hereby corrected as shown below:

IN THE CLAIMS

Col. 7, lines 58 and 69; Col. 8, line 63:
Claim 1, lines 3 and 9; Claim 6, line 4:   delete "general"

Col. 8, line 62:
Claim 6, line 3:   "(N-$C_1C_6$-alkyl) should read --(N-$C_1$-$C_6$-alkyl)--

Col. 8, line 65:
Claim 7, line 1:   "$a^1$" should read --$A^1$--

Signed and Sealed this

Twenty-first Day of January, 1992

Attest:

HARRY F. MANBECK, JR.

*Attesting Officer*          *Commissioner of Patents and Trademarks*